United States Patent
Wagner et al.

(10) Patent No.: US 10,813,871 B2
(45) Date of Patent: Oct. 27, 2020

(54) NON-CHEMICAL SMOOTHING AND DE-CURLING AGENTS

(71) Applicant: Henkel AG & Co. KGaA, Duesseldorf (DE)

(72) Inventors: Aileen Wagner, Hamburg (DE); Matthias Schweinsberg, Langenfeld (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 9 days.

(21) Appl. No.: 15/662,288

(22) Filed: Jul. 28, 2017

(65) Prior Publication Data
US 2018/0055753 A1   Mar. 1, 2018

(30) Foreign Application Priority Data

Aug. 30, 2016  (DE) .................. 10 2016 216 312

(51) Int. Cl.
| | |
|---|---|
| *A61K 8/65* | (2006.01) |
| *A61K 8/64* | (2006.01) |
| *A61K 8/891* | (2006.01) |
| *A45D 7/02* | (2006.01) |
| *A61K 8/04* | (2006.01) |
| *A61K 8/33* | (2006.01) |
| *A61K 8/34* | (2006.01) |
| *A61K 8/41* | (2006.01) |
| *A61K 8/44* | (2006.01) |
| *A61K 8/58* | (2006.01) |
| *A61Q 5/06* | (2006.01) |
| *A45D 7/00* | (2006.01) |

(52) U.S. Cl.
CPC .................. *A61K 8/65* (2013.01); *A45D 7/02* (2013.01); *A61K 8/046* (2013.01); *A61K 8/33* (2013.01); *A61K 8/34* (2013.01); *A61K 8/345* (2013.01); *A61K 8/416* (2013.01); *A61K 8/44* (2013.01); *A61K 8/585* (2013.01); *A61K 8/64* (2013.01); *A61K 8/645* (2013.01); *A61K 8/891* (2013.01); *A61Q 5/06* (2013.01); *A45D 2007/005* (2013.01)

(58) Field of Classification Search
None
See application file for complete search history.

(56) References Cited

U.S. PATENT DOCUMENTS

| | | | |
|---|---|---|---|
| 5,059,414 A | 10/1991 | Dallal et al. | |
| 5,213,799 A | 5/1993 | Goring et al. | |
| 5,618,524 A * | 4/1997 | Bolich, Jr. | ............. A61K 8/046 424/70.12 |
| 2005/0287083 A1* | 12/2005 | Emmerling | .............. A61K 8/03 424/47 |
| 2011/0059192 A1* | 3/2011 | Glynn | .................... A61K 8/678 424/727 |

FOREIGN PATENT DOCUMENTS

| | | |
|---|---|---|
| EP | 2135596 A1 | 12/2009 |
| GB | 2206048 A | 12/1988 |
| JP | H11222415 A | 8/1999 |
| WO | 9317687 A1 | 9/1993 |
| WO | 02060397 A1 | 8/2002 |
| WO | 2014023782 A1 | 2/2014 |
| WO | 2014137739 A1 | 9/2014 |

OTHER PUBLICATIONS

Intellectual Property Office, Search Report under Section 17(5) for United Kingdom Patent Application No. GB1713687.0 dated May 23, 2018.

* cited by examiner

*Primary Examiner* — David J Blanchard
*Assistant Examiner* — Sarah J Chickos
(74) *Attorney, Agent, or Firm* — Lorenz & Kopf, LLP

(57) ABSTRACT

The present disclosure relates to a multi-phase liquid agent for the non-chemical smoothing and de-curling of keratin fibers, in particular human hair, which has an aqueous-alcoholic phase and a non-aqueous phase existing separately therefrom and which can be applied as a spray, and a method for non-chemical smoothing or de-curling of keratin fibers using the agent.

20 Claims, No Drawings

NON-CHEMICAL SMOOTHING AND DE-CURLING AGENTS

CROSS-REFERENCE TO RELATED APPLICATION

This application claims priority to German Application No. 10 2016 216 312.4, filed Aug. 30, 2016, which is hereby incorporated in its entirety by reference.

TECHNICAL FIELD

The present disclosure relates to a multi-phase liquid agent for the non-chemical smoothing and de-curling of keratin fibers, in particular human hair, which has an aqueous-alcoholic phase and a non-aqueous phase existing separately therefrom and which can be applied as a spray, and a method for the non-chemical smoothing or de-curling of keratin fibers using the agent.

BACKGROUND

In principle, all animal hair, e.g. wool, horse hair, angora hair, furs, feathers and products or textiles made therefrom can be used as keratin-containing fibers. However, the disclosure is preferably used in the context of smoothing curly human hair and wigs produced therefrom.

A permanent deformation of keratin-containing fibers is usually carried out in such a way that the fiber is mechanically deformed and the deformation is fixed by suitable additives. The fiber is treated with a keratin-reducing preparation before and/or after this deformation. After a rinsing operation, the fiber is then treated with an oxidizing agent preparation in the so-called fixing step, rinsed, and freed from the shaping aids (winders, papillots) after or during the fixing step. When a mercaptan is used as a keratin reducing component, e.g., ammonium thioglycolate, this part of the disulfide bridges of the keratin molecule cleaves to —SH groups, so that the keratin fiber is softened. During subsequent oxidative fixation, disulfide bridges are again bound in the hair keratin, so that the keratin structure is fixed in the predetermined deformation. Alternatively, it is known to use sulfite instead of the mercaptans for hair shaping. Through hydrogen sulfite solutions and/or sulfite solutions and/or disulfite solutions, disulfide bridges of the keratin are cleaved in a sulfitolysis according to the equation

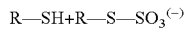

and thus a softening of the keratin fiber is achieved. Hydrogen sulfite, sulfite or disulfite-containing reducing agents do not have the strong inherent odor of the mercaptan-containing agents. The cleavage can be reversed as described above in a fixing step with the aid of an oxidizing agent to form new disulfide bridges.

The permanent smoothing of keratin-containing fibers can be achieved analogously by the use of keratin-reducing and -oxidizing compositions. In a corresponding method, the curled hair is either wound onto winders having a large diameter of usually more than 15 mm, or the hair is combed smoothly under the action of the keratin-reducing composition. Instead of the winder, it is also possible to smooth out the fiber onto a smoothing board. Smoothing boards are usually rectangular panels e.g., made of plastic. Preferably, the fiber is thereby wetted with the keratin-reducing preparation. A further possibility for hair smoothing is the smoothing with a hot iron.

The above-described permanent smoothing includes, as described, a chemical reduction and thus possibly permanent damage to the keratin fibers. In particular, when enhanced smoothing is to be achieved, this is usually also accompanied by increased damage to the keratin-containing fiber. This is not always desirable and therefore non-chemical methods for the smoothing of hair are also known, wherein usually a creamy emulsion, which contains care substances and conditioning substances is applied to the hair with a brush or similar and the hair is then smoothed, for example, with a flat iron. However, this process is relatively time-consuming and cumbersome, since the cream must first be evenly distributed in the hair with a brush, and the smoothing effect is not always satisfactory. It would therefore be desirable to have an easy-to-use non-chemical smoothing agent which has a long-lasting smoothing effect, thus allowing a greater number of hair washes without losing the smoothing.

It is therefore an object as contemplated herein to provide a non-chemical smoothing agent for keratin-containing fibers, in particular for human hair, which has an excellent smoothing effect and is easy to use.

BRIEF SUMMARY

A multi-phase liquid agent for the non-chemical smoothing and de-curling of keratin fibers is provided herein. The agent has a pH value of from about 2 to about 10. The agent has an aqueous-alcoholic phase and a non-aqueous phase existing separately therefrom. The agent includes (a) at least one care substance liquid at 20° C. in a total quantity of from about 0.3 to about 15% by weight. The agent further includes (b) at least one cosmetically acceptable alcohol in a total amount of from about 5 to about 35% by weight. The agent further includes (c) from about 30 to about 80% by weight of water. The agent further includes (d) at least one cosmetic oil liquid at 20° C. and is selected from cyclopentasiloxane, cyclohexasiloxane, dimethylpolysiloxane, methylphenylpolysiloxane, hexamethyldisiloxane, octamethyltrisiloxane and decamethyltetrasiloxane, and mixtures of two or more thereof, in a total amount of from about 5 to about 40% by weight. The liquid agent includes about 0.1% by weight or less of solid fatty substances at 20° C. The quantity value for each component is based on the total weight of the liquid agent.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

Surprisingly, a non-chemical smoothing agent has now been found, which is recognizable in several phases, in particular two-phases, and which has a water-like viscosity and contains a high proportion of care and/or conditioning substances, can be applied simply by spraying and has an excellent smoothing effect for non-chemical smoothing agents.

The present disclosure relates to:
1. A multi-phase liquid agent for the non-chemical smoothing and de-curling of keratin fibers, in particular human hair, having a pH value of from about 2 to about 10 and has an aqueous-alcoholic phase and a non-aqueous phase existing separately therefrom, with the following ingredients:

(a) at least one care substance liquid at 20° C. in a total quantity of from about 0.3 to about 15% by weight,
(b) at least one cosmetically acceptable alcohol in a total amount of from about 5 to about 35% by weight,
(c) from about 30 to about 80% by weight of water and
(d) at least one cosmetic oil liquid at 20° C. and is selected from cyclopentasiloxane, cyclohexasiloxane, dimethylpolysiloxane, methylphenylpolysiloxane, hexamethyldisiloxane, octamethyltrisiloxane and decamethyltetrasiloxane, and mixtures of two or more thereof, in a total amount of from about 5 to about 40% by weight, wherein:
  the liquid agent contains about 0.1% by weight or less, preferably no solid fatty substances at 20° C., and
  the quantity specifications relate in each case to the total weight of the liquid agent.
2. Agent according to point 1, wherein it is a two-phase agent.
3. Agent according to point 1 or 2, wherein the agent further contains lysine, preferably in a total amount of from about 0.01 to about 5% by weight, more preferably from about 0.2 to about 2% by weight, based in each case on the total weight of the liquid agent.
4. Agent according one of the preceding points, wherein the agent has a viscosity (Brookfield RVDV-II+, 20° C., spindle 1, 100 rpm) of from about 0 to about 2000 mPa·s, preferably from about 0.2 to about 1000 mPa·s, more preferably from about 0.5 to about 500 mPa·s.
5. Agent according to one of the preceding points, wherein the cosmetic oil (d) comprises cyclopentasiloxane, octamethyltrisiloxane or a mixture thereof or comprises cyclopentasiloxane, octamethyltrisiloxane or a mixture thereof.
6. Agent according to one of the preceding points, wherein at least one component selected from the group consisting of protein hydrolyzates, derivatives of protein hydrolyzates, quaternary ammonium compounds, glycerol and mixtures thereof is contained as the care substance (a).
7. Agent according to one of the preceding points, wherein an alcohol having 1 to 4 carbon atoms or a mixture thereof is contained as the alcohol (b), preferably ethanol and/or isopropanol, more preferably ethanol.
8. Agent according to any one of the preceding points, wherein the aqueous-alcoholic phase and the non-aqueous phase are present in a weight ratio of from about 60 to about 90 (aqueous-alcoholic phase) to from about 10 to about 40 (non-aqueous phase).
9. Agent according to one of the preceding points, which contains about 0.1% by weight or less, based on the total weight of the liquid agent, preferably no keratin-reducing substances.
10. Agent according to one of the preceding claims, which contains about 0.05% by weight or less based on the total weight of the liquid agent, preferably no formaldehyde.
11. Agent according to one of the preceding points, which is made up as a spray.
12. Cosmetic, non-medical method for the non-chemical smoothing or de-curling of keratin fibers, in particular of human hair, in which the liquid agent according to one of the preceding claims is sprayed onto the hair and distributed in the hair, the hair is subsequently dried and then is smoothed via mechanical and/or heating action.
13. Method according to point 12, having the following steps:
a. Washing the hair with a shampoo,
b. Applying the smoothing agent to the hair by spraying without prior drying of the hair,
c. Smoothing the hair by mechanical and/or heating action.
14. Method according to point 14, wherein after step c., no washing of the hair takes place.
15. Kit-of-parts comprising, as a part, the aqueous-alcoholic phase of the agent according to any one of points 1 to 10 and as another part the non-aqueous phase(s) of the agent according to one of points 1 to 10.

As contemplated herein, the term "liquid" refers to the aggregate state at 1013 mbar and 20° C. "liquid" means that the agent has a viscosity such that it can be applied well by spraying. The agent preferably has a viscosity from about 0 to about 2000 mPa·s, preferably from about 0.1 to about 1500 mPa·s, more preferably from about 0.2 to about 1000 mPa·s, still more preferably from about 0.5 to about 500 mPa·s (Brookfield RVDV-II+, 20° C., spindle 1, 100 rpm). The viscosity ranges specified above refer to the viscosity of the agent determined by employing a Brookfield viscometer, which is mixed in determining viscosity according to Brookfield. However, the viscosity ranges specified above also relate both to the aqueous-alcoholic phase and to the non-aqueous phase when the viscosities of these individual phases are measured.

The term keratin fibers as contemplated herein comprises furs, wool and feathers, but in particular human hair.

The smoothing agent is a multi-phase liquid agent, wherein a two-phase agent is preferred. Such two-phase and multi-phase systems are systems in which at least two separate, continuous phases are present. Examples of such systems are preparations which have the following phases:
  an aqueous-alcoholic phase, and a non-aqueous phase, which are separate from one another
  an aqueous-alcoholic phase and two non-aqueous, mutually immiscible phases, each of which is present separately.
In the context of the present disclosure, systems in which only one continuous phase is present, such as oil-in-water or water-in-oil emulsions, are not two-phase or multi-phase systems.

The smoothing agent has a pH value of from about 2 to about 10 measured at 20° C. The pH value is more preferably in the range of from about 3 to about 8, more preferably in the range of from about 4 to about 6.

The liquid smoothing agent contains, as an essential constituent (a), liquid care substances at 20° C. in a total amount of from about 0.3 to about 15% by weight, based on the total weight of the liquid smoothing agent. The total amount of the care substance (a) is preferably from about 0.5 to about 10% by weight, more preferably from about 1 to about 5% by weight. In the present disclosure, substances which are frequently classified as conditioning substances are also included among the care substances (a). Preference is given to the care substances (a) protein hydrolyzates, derivatives of protein hydrolyzates, quaternary ammonium compounds, glycerin and mixtures thereof. Although the cosmetic oil of the component (d) has a nourishing effect, the components (d) which form the non-aqueous phase are not counted among the care substances (a) in this disclosure.

The useful care substances (a) include, in particular, protein hydrolyzates. Protein hydrolyzates are product mixtures which are obtained by acidic, basic or enzymatically catalyzed degradation of proteins. As contemplated herein, protein hydrolyzates of both plant and animal origin can be used.

Animal protein hydrolyzates are, for example, elastin, collagen, keratin, silk and milk protein hydrolyzates, which can also be present in the form of salts. Such products are marketed, for example, under the names Nutrilan® (BASF SE), Lamequat® (BASF SE), ProSina (Croda) and Croquat (Croda).

Preferred animal protein hydrolyzate products are, for example, Nutrilan® Keratin W PP and ProSina as well as mixtures thereof.

As contemplated herein, it is also possible to use protein hydrolyzates of plant origin, e.g., soya, almond, pea, rice, potato, oat, corn and wheat protein hydrolyzates.

Suitable derivatives are in particular also quaternized protein hydrolyzates. Examples of this compound class are those described under the names Lamequat® L (CTFA designation: Lauryldimonium Hydroxypropylamino Hydrolyzed Animal Protein), Croquat® WKP and Gluadin® WQ products on the market.

The protein hydrolyzates or derivatives thereof are preferably present in the compositions in amounts of from about 0.1 to about 5% by weight, based on the total amount of the agent. Amounts of from about 0.5 to about 2.5% by weight are more preferred.

Quaternary ammonium compounds (a) are also preferred among the usable care substances. These are often also referred to as conditioning components. Preference is given to ammonium halides, in particular chlorides and bromides, such as alkyltrimethylammonium chlorides, dialkyldimethylammonium chlorides and trialkylmethylammonium chlorides, for example cetyltrimethylammonium chloride, stearyltrimethylammonium chloride, distearyldimethylammonium chloride, lauryldimethylammonium chloride, lauryldimethylbenzylammonium chloride and tricetylmethylammonium chloride. Preferred quaternary ammonium compounds are commercially available under the names Dehyquart® A-CA (Trimethyl Hexadecyl Ammonium Chloride, INCI: Cetrimonium chlorides), Dehyquart® E-CA INCI: Hydroxycetyl hydroxyethyl dimonium chlorides) and Dehyquart® SP (INCI: Quaternium-52) (in each case BASF), wherein a mixture of these is preferably used. The quaternary ammonium compounds are preferably contained in a total amount of from about 0.1 to about 5% by weight, preferably from about 0.2 to about 3% by weight, more preferably from about 0.5 to about 2.5% by weight, based on the total amount of the smoothing agent.

Glycerin is also preferably among the usable care substances (a). The glycerin is preferably contained in a total amount of from about 0.1 to about 5% by weight, preferably from about 0.2 to about 3% by weight, more preferably from about 0.5 to about 2.5% by weight, based on the total amount of the smoothing agent. Within the scope of this application, glycerin is counted as a care substance (a) and not as an alcohol (b).

In preferred embodiments as contemplated herein, the total amount of the protein hydrolyzates, quaternary ammonium compounds and glycerin contained is in the range from about 0.3 to about 15% by weight, more preferably from about 0.5 to about 10% by weight, based on the total amount of the smoothing agent.

Further known ingredients can be included in the agent as a care substance (a) in addition to those already mentioned and partially replace these. In preferred embodiments as contemplated herein, further care substances are only included in small amounts or not at all.

Suitable further care substances (a) of the aqueous-alcoholic phase can be a vitamin, a provitamin, a vitamin precursor and/or one of its derivatives. Such vitamins, provitamins and vitamin precursors which are usually assigned to the groups A, B, C, E, F and H are preferred.

As contemplated herein, the non-aqueous phase is formed from the at least one cosmetic oil liquid at 20° C., selected from cyclopentasiloxane, cyclohexasiloxane, dimethylpolysiloxane and methylphenylpolysiloxane, hexamethyldisiloxane, octamethyltrisiloxane and decamethyltetrasiloxane, and mixtures of two or more thereof. The compounds mentioned are substances with low, water-like kinematic viscosity measured at 25° C., from about 0.5 to about 2 cSt. The viscosities are determined according to the ball-fall method according to the method "British standard 188". Comparable values are obtained using manufacturers' test specifications analogous to the "British standard 188", such as the "CTM 0577" from Dow Corning Corporation Particularly preferably, the at least one cosmetic oil (d) comprises cyclopentasiloxane, octamethyltrisiloxane or a mixture thereof or consists of cyclopentasiloxane, octamethyltrisiloxane or a mixture thereof. More preferably, the cosmetic oil (d) comprises a mixture of cyclopentasiloxane and octamethyltrisiloxane. Also especially preferably, the non-aqueous phase is constituted of cyclopentasiloxane, octamethyltrisiloxane or a mixture thereof, i.e., the smoothing agent as contemplated herein, contains no further constituent which belongs to the non-aqueous phase.

The total amount of the cosmetic oil (d) is preferably in the range of from about 10 to about 30% by weight, more preferably from about 15 to about 25% by weight, more preferably from about 18 to about 22% by weight, based on the total amount of the smoothing agent.

Further known cosmetic oils can be contained in the agent as a cosmetic oil (d) in addition to those already mentioned and partially replace them. In preferred embodiments as contemplated herein, further cosmetic oils or the non-aqueous phase-forming constituents are contained only in small amounts or not at all.

Suitable further usable oils liquid at 20° C. are selected from the esters of linear or branched saturated or unsaturated fatty alcohols having from about 2 to about 30 carbon atoms with linear or branched saturated or unsaturated fatty acids having from about 2 to about 30 carbon atoms, which can be hydroxylated. These include cetyl-2-ethylhexanoate (e.g., Schercemol® CO ester), 2-hexyldecyl stearate (e.g., Eutanol® G 16 S), 2-hexyldecyl laurate, isodecyl neopentanoate, isononyl isononanoate, 2-ethylhexyl palmitate (e.g., Cegesoft®C 24) and 2-ethylhexyl stearate (e.g., Cetiol® 868). Also suitable are isopropyl myristate, isopropyl palmitate, isopropyl stearate, isopropyl isostearate, isopropyloleate, isooctyl stearate, isononyl stearate, isocetyl stearate, isononyl isononanoate, isotridecyl isononanoate, cetearyl isononanoate, 2-ethylhexyl laurate, 2-ethylhexylisostearate, 2-ethylhexyl cocoate, 2-octyldodecyl palmitate, butyloctanoate-2-butyloctanoate, diisotridecyl acetate, n-butyl stearate, n-hexyl laurate, n-decyloleate, oleyl oleate, oleyl erucate, erucyl oleate, erucyl erucate, ethylene glycol diolate and ethylene glycol dipalmitate.

Further suitable oils are selected from natural and synthetic hydrocarbons, more preferably from mineral oils, paraffin oils, $C_{18}$-$C_{30}$ isoparaffins, in particular isoeicosan, polyisobutenes and polydecenes which are available, for example, under the name Emery® 3004, 3006, 3010 or under the name Ethylflo® from Albemarle or Nexbase® 2004G from Nestlé, further selected from $C_8$-$C_{16}$ isoparaffins, especially from isodecane, isododecane, isotetradecane and isohexadecane, and mixtures thereof, and 1,3-di-(2-ethylhexyl) cyclohexane (available, for example, under the trade name Cetiol S from BASF SE).

Further suitable oils as contemplated herein are selected from the benzoic acid esters of linear or branched $C_{8-22}$ alkanols. Particular preference is given to benzoic acid $C_{12}$-$C_{15}$-alkyl esters, e.g., commercially available as Finsolv® TN, benzoic acid isostearyl ester, e.g., commercially available Finsolv® SB, ethylhexyl benzoate, e.g., commercially available as Finsolv® EB, and benzoic acid octyl dodecyl esters, e.g., commercially available as Finsolv® BOD.

Further suitable cosmetic oils are selected from the triglycerides (=triple esters of glycerin) of linear or branched, saturated or unsaturated, optionally hydroxylated $C_{8-30}$ fatty acids, in so far as they are liquid at 20° C. Particular preference is given to the use of natural oils, e.g. amaranth oil, apricot kernel oil, argan oil, avocado oil, babassu oil, cottonseed oil, borage seed oil, camelina oil, thistle oil, peanut oil, pomegranate kernel oil, grapefruit seed oil, hemp oil, hazelnut oil, locust seed oil, jojoba oil, linseed oil, macadamian nut oil, corn oil, almond oil, marilla oil, evening primrose oil, olive oil, palm oil, palm kernel oil, paranut oil, pecan oil, peach kernel oil rape seed oil, castor oil, sanddorn fruit oil, sand kernel oil, sesame oil, soybean oil, sunflower oil, grape seed oil, walnut oil, wild rose oil, wheat germ oil, and the liquid fractions of coconut oil and the like. However, preference is also given to synthetic triglyceride oils, in particular capric/caprylic triglycerides, e.g., the commercial product Myritol® 318 (BASF SW) with unbranched fatty acid residues and glyceryl triisosarin with branched fatty acid residues.

Further suitable cosmetic oils are selected from the dicarboxylic acid esters of linear or branched $C_2$-$C_{10}$-alkanols, in particular diisopropyl adipate, di-n-butyl adipate, di-(2-ethylhexyl) adipate, dioctyl adipate, diethyl/di-n-butyl/dioctyl sebacate, diisopropyl sebacate, dioctyl malate, dioctyl maleate, dicaprylyl maleate, diisooctyl succinate, di-2-ethylhexyl succinate and di-(2-hexyldecyl) succinate.

Further suitable cosmetic oils are selected from the addition products of 1 to 5 propylene oxide units to monohydric or polyhydric $C_{8-22}$ alkanols such as octanol, decanol, decanediol, lauryl alcohol, myristyl alcohol and stearyl alcohol, e.g., PPG-2 myristyl ether and PPG-3 myristyl ether (e.g., Witconol® APM).

Further suitable cosmetic oils are selected from the addition products of at least 6 ethylene oxide units and/or propylene oxide units to mono- or polyhydric $C_{3-22}$ alkanols such as glycerin, butanol, butanediol, myristyl alcohol and stearyl alcohol, which can be esterified if desired, e.g., PPG-14-butyl ether (e.g., Ucon Fluid® AP), PPG-9-butyl ether (e.g., Breox® B25), PPG-10-butanediol (e.g., Macol® 57), PPG-15-stearyl ether (e.g., Arlamol® E) and glycereth-7-diisononanoate.

Further suitable cosmetic oils are selected from the $C_8$-$C_{22}$ fatty alcohol esters of monovalent or polyvalent $C_2$-$C_7$-hydroxycarboxylic acids, in particular the esters of glycolic acid, lactic acid, malic acid, tartaric acid, citric acid and salicylic acid. Such esters based on linear $C_{14/15}$ alkanols, for example, for example, $C_{12}$-$C_{15}$ alkyl lactate and $C_{12/13}$ alkanols branched in 2-position, are vailable under the trade name Cosmacol® from Nordmann, Rassmann GmbH & Co, Hamburg, in particular the commercial products Cosmacol® ESI, Cosmacol® EMI and Cosmacol® ETI.

Further suitable cosmetic oils are selected from the symmetrical, unsymmetrical or cyclic esters of carbonic acid with $C_{3-22}$ alkanols, $C_{3-22}$ alkanediols or $C_{3-22}$ alkanetriols, e.g., dicaprylyl carbonate (Cetiol® CC) or the esters according to the teaching of DE 19756454 A1, in particular glycerin carbonate.

Further cosmetic oils which may be suitable are selected from the esters of dimeric unsaturated $C_{12}$-$C_{22}$ fatty acids (dimer fatty acids) with monovalent linear, branched or cyclic $C_2$-$C_{18}$ alkanols or with polyhydric linear or branched $C_2$-$C_6$ alkanols.

In particularly preferred embodiments, the agent contains lysine, preferably L-lysine, as a further constituent. It was surprisingly determined that the smoothing properties were yet again significantly improved in the presence of L-lysine. Preference is given to embodiments in which lysine, preferably L-lysine, is contained in a total amount of from about 0.01 to about 5% by weight, more preferably from about 0.2 to about 2% by weight, based in each case on the total weight of the liquid agent.

The smoothing agent contains, as a component (b), at least one cosmetically acceptable alcohol in a total amount of from about 5 to about 35% by weight, based on the total weight of the liquid agent, together with water as component (c), the cosmetic carrier forms of the aqueous-alcoholic phase. The alcohol content is preferably from about 10 to about 30% by weight, more preferably from about 15 to about 25% by weight, based in each case on the total weight of the liquid agent. The alcohol used is preferably ethanol and/or isopropanol, wherein ethanol is preferred.

The water content (c) of the smoothing agent is from about 30 to about 80% by weight, preferably from about 40 to about 65% by weight, more preferably from about 45 to about 55% by weight, based on the total weight of the liquid agent.

The aqueous-alcoholic phase and the non-aqueous phase are preferably present in a weight ratio of from about 60 to about 90 (aqueous-alcoholic phase) to from about 10 to about 40 (non-aqueous phase), more preferably from about 70 to about 85 (aqueous-alcoholic phase) to from about 15 to about 30 (non-aqueous phase), yet more preferably from about 78 to about 85 (aqueous-alcoholic phase) to from about 15 to about 22 (non-aqueous phase).

The agent is a non-chemical smoothing agent which therefore preferably contains about 0.1% by weight or less, preferably no keratin-reducing substances. Furthermore, the smoothing agent as contemplated herein preferably contains about 0.05% by weight or less, preferably no formaldehyde, which is occasionally contained in known smoothing agents or is formed over time.

The agents may also contain customary constituents of cosmetic agents, such as, for example, preservatives, perfumes, fragrances or pH adjusters. Emulsifiers may also be present in smaller amounts, or the components already mentioned may have an emulsifying effect in order to bring perfume or other constituents into the aqueous phase as long as the agent forms a total of at least two separate phases.

Furthermore, it may be preferred to color the individual phases with dyes in order to achieve a particularly good optical appearance of the agent. These dyes are preferably soluble only in the aqueous phase or only in at least one non-aqueous phase in an amount which makes a corresponding coloration appear visible to the observer. It is also possible to dye both the non-aqueous phase and the aqueous phase with different dyes, preferably in different colors. However, the sole coloring of a non-aqueous phase is preferred.

The smoothing agent contains fatty substances solid at 20° C. in a total amount of at most 0.1% by weight or less, based on the total weight of the agent. Particular preference is not given to fatty substances which are solid at 20° C. The absence or substantial absence of the fatty substances can ensure that no undesirable residues remain on the hair after the smoothing treatment.

The fatty substances solid at 20° C. or higher temperatures and which are included in agents only in a total amount of at most about 0.1% by weight or less, based on the total weight of the agent, and preferably not at all, are, for example, coconut fatty acid glycerol mono-, di- and triesters, butyrospermum parkii (shea butter), esters of saturated monovalent $C_8$-$C_{18}$ alcohols with saturated $C_{12}$-$C_{18}$ monocarboxylic acids, such as, for example, stearyllaurate, cetearyl stearate, cetyl palmitate and myristyl myristate, furthermore linear saturated alkanols with 12-30 carbon atoms, in particular with 16-22 carbon atoms, in particular cetyl alcohol, stearyl alcohol, arachidyl alcohol, behenyl alcohol and lanolin alcohol or mixtures of these alcohols such as are obtainable in the technical hydrogenation of vegetable and animal fatty acids, furthermore esters and, in particular, partial esters of a polyol having 2 to 6 carbon atoms and linear saturated fatty acids having 12 to 30 C-atoms which can be hydroxylated. Such esters or partial esters are, for example, the mono- and diesters of glycerol or ethylene glycol or the monoesters of propylene glycol with linear saturated $C_{12}$-$C_{30}$-carboxylic acids which can be hydroxylated, in particular those with palmitic and stearic acid, the sorbitan mono-, di- or triesters of linear saturated $C_{12}$-$C_{30}$-carboxylic acids, which can be hydroxylated, for example, those of myristic acid, palmitic acid, stearic acid or mixtures of these fatty acids, the pentaerythritylmono-, di-, tri- and tetra-esters and the methylglucosemono- and diesters of linear saturated $C_{12}$-$C_{30}$-carboxylic acids, which can be hydroxylated, for example, the mono-, di-, tri- and tetraesters of pentaerythritol with linear saturated fatty acids having 12-30 carbon atoms, which can be hydroxylated, and further esters of a saturated monohydric $C_{16}$-$C_{60}$ alkanol and a saturated $C_8$-$C_{36}$ monocarboxylic acid, for example cetyl behenate, stearyl behenate and $C_{20}$-$C_{40}$alkyl stearate, glycerol triesters of saturated linear $C_{12}$-$C_{30}$-carboxylic acids, which can be hydroxylated, hardened castor oil, candelilla wax, carnauba wax, beeswax, saturated linear $C_{14}$-$C_{36}$-carboxylic acids, and mixtures of the abovementioned substances.

The smoothing agent is applied to the hair by spraying. For this purpose, it is preferably made up as a spray in a corresponding container. The container should preferably be shaken before spraying. It is also possible to make up the smoothing agent as a kit-of-parts, wherein the aqueous-alcoholic phase and the non-aqueous phase are present separately and are mixed just before the application to the hair and then sprayed.

The present disclosure also relates to a method for the non-chemical smoothing or de-curling of keratin fibers, in particular of human hair, in which the liquid agent according to one of the preceding claims is sprayed onto the hair and distributed in the hair, the hair is then dried and then is smoothed by mechanical or heating action. The method as contemplated herein has the advantage in that using an aid such as a brush or the like is no longer required because it is easy to spray on due to the low, water-like viscosity and penetrates the hair strands well.

The method for smoothing keratin fibers using the smoothing agent also ensures a markedly reduced total time for the smoothing of hair. More specifically, a preferred method of smoothing keratin fibers as contemplated herein may have the following steps:

a. Washing the hair with a shampoo,
b. Applying the smoothing agent to the hair by spraying without prior drying of the hair,
c. Smoothing the hair by mechanical and/or heating action. Preferably, no further washing of the hair is carried out after the step c., the smoothing of the hair. The method for smoothing keratin fibers is thus significantly shortened with respect to conventional smoothing methods with non-chemical smoothing agents.

Conventional smoothing methods for non-chemical smoothing usually include the steps: Washing the hair with a shampoo, drying the hair by blow drying, applying the smoothing agent with a brush strand by strand, drying the hair by blow drying, smoothing, again washing with a shampoo and treating with a conditioner and drying blow dryers. On the other hand, the smoothing method as contemplated herein has fewer treatment steps and also the application of the smoothing agent itself can take place faster due to the low viscosity and easy spraying. A time saving of more than 30 minutes resulted in comparative tests carried out. At the same time, a smoothing effect was obtained which is comparable to the non-chemical smoothing agents known from top products. This refers both to the appearance of the hair immediately after the smoothing as well as to the duration of the smoothing effect. For example, an excellent smoothing of the hair could be achieved through the agent, which endured up to 36 hair washes with no substantial loss of the smoothing effect.

With respect to preferred embodiments of the method, the same is true as with respect to the liquid smoothing agent, necessary changes being made.

Table Overview

The composition of some preferred fluid smoothing agents can be found in the following tables (specified in % by weight, based on the total weight of the cosmetic agent, unless otherwise specified).

TABLE 1

|  | Formula 1 | Formula 2 | Formula 3 | Formula 4 |
| --- | --- | --- | --- | --- |
| Care substance (a) | 0.3 to 15 | 0.5 to 10 | 1 to 5 | 1 to 5 |
| Alcohol (b) | 5 to 35 | 10 to 30 | 15 to 25 | 15 to 25 |
| Water (c) | 30 to 80 | 40 to 65 | 45 to 55 | 45 to 55 |
| Cosmetic oil (d) | 5 to 40 | 5 to 30 | 15 to 25 | 18 to 22 |
| Misc | ad 100 | ad 100 | ad 100 | ad 100 |
|  | Formula 5 | Formula 6 | Formula 7 | Formula 8 |
| (a) Protein hydrolyzate or derivative thereof | 0.1 to 5 | 0.2 to 4 | 0.3 to 3 | 0.5 to 2.5 |
| (a) Quaternary ammonium compound | 0.1 to 5 | 0.2 to 4 | 0.3 to 3 | 0.5 to 2.5 |
| (a) Glycerin | 0.1 to 5 | 0.2 to 4 | 0.3 to 3 | 0.5 to 2.5 |
| (b) Ethanol and/or isopropanol | 5 to 35 | 10 to 30 | 15 to 25 | 15 to 25 |
| Water (c) | 30 to 80 | 40 to 65 | 45 to 55 | 45 to 55 |

TABLE 1-continued

| | | | | |
|---|---|---|---|---|
| (d) Cyclopentasiloxane, cyclohexasiloxane, dimethylpolysiloxane, methylphenylpolysiloxane, hexamethyldisiloxane, octamethyltrisiloxane, decamethyltetrasiloxane or a mixture of two or more thereof | 5 to 40 | 5 to 30 | 15 to 25 | 18 to 22 |
| Misc | ad 100 | ad 100 | ad 100 | ad 100 |

| | Formula 9 | Formula 10 | Formula 11 | Formula 12 |
|---|---|---|---|---|
| (a) Keratin, collagen and/or wheat protein hydrolyzate | 0.1 to 5 | 0.2 to 4 | 0.3 to 3 | 0.5 to 2.5 |
| (a) INCI: Cetrimonium chloride, INCI: Hydroxycetyl hydroxyethyl dimonium chloride and/or INCI: Quaternium-52 | 0.1 to 5 | 0.2 to 4 | 0.3 to 3 | 0.5 to 2.5 |
| (a) Glycerin | 0.1 to 5 | 0.2 to 4 | 0.3 to 3 | 0.5 to 2.5 |
| Ethanol (b) | 5 to 35 | 10 to 30 | 15 to 25 | 15 to 25 |
| Water (c) | 30 to 80 | 40 to 65 | 45 to 55 | 45 to 55 |
| (d) Cyclopentasiloxane | 4.5 to 30 | 4.5 to 25 | 10 to 20 | 13 to 27 |
| (d) Octamethyltrisiloxane | 0.5 to 15 | 0.5 to 10 | 2 to 8 | 3 to 7 |
| Misc | ad 100 | ad 100 | ad 100 | ad 100 |

"Misc" is understood to mean further conventional constituents, such as, for example, chelating agents for heavy metal ions, preservatives, fragrances, perfumes, pH regulators.

Preferably, "Misc" does not include any or only small amounts of fatty substances solid at 20° C. so that the agent contains a total of 0.1% by weight or less or no fatty substances solid at 20° C.

Preferably, "Misc" also contains no or only small amounts of keratin-reducing substances and formaldehyde, so that the agent contains a total of 0.1% by weight or less or no keratin-reducing substances and 0.05% by weight or less or no formaldehyde.

Examples

The smoothing agents shown in Table 1 below were prepared. Unless stated otherwise, the amounts specified are percentage by weight. Examples 1 and 2 are liquid, two-phase smoothing agents as contemplated herein. Comparative Example 1 is a conventional creamy, single phase smoothing agent.

TABLE 2

| Component | Ex. 1 | Ex. 2 | Comp. Ex. 1 |
|---|---|---|---|
| Aqueous phase | 80 | 80 | Creamy emulsion, no separate phases |
| Water, demineralized | 48.688 | 49.24772 | 47.76 |
| D&C VIOLET NO 2 EXTERNAL | — | 0.00020 | — |
| 307002 D&C Red No. 33 | — | 0.000080 | — |
| Polyquaternium-10 | — | — | 1.2 |
| Polyquaternium-7 | — | — | 2.0 |
| Lysine HCl | 0.80 | — | — |
| Glycerin 99.5% | 1.60 | 1.60 | 1.40 |
| Na benzoate | — | — | 0.40 |
| Dehyquart ® A CA | 0.80 | 0.80 | 1.00 |
| Citric acid monohydrate | — | — | 0.05 |

TABLE 2-continued

| Component | Ex. 1 | Ex.2 | Comp. Ex. 1 |
|---|---|---|---|
| Paraffinum liquidum | — | — | 1.20 |
| PEG-7 glyceryl cocoate | — | — | 0.49 |
| Perfume 07-10129 | — | — | 0.40 |
| Water, demineralized | — | — | 39.00 |
| Dehyquart ® E CA | 0.80 | 0.80 | — |
| Dehyquart ® SP | 0.80 | 0.80 | — |
| Nutrilan ® Keratin W PP | 0.40 | 0.40 | 0.50 |
| Gluadin ® WQ PP | 0.80 | 0.80 | — |
| Lamequat ® L | 0.80 | 0.80 | — |
| Croquat ® WKPS-LQ-(WD) | 0.16 | 0.16 | — |
| ProSina ® | 0.08 | 0.08 | — |
| Vitamin C | — | — | 0.05 |
| PEG-7 glyceryl cocoate | 1.60 | 1.60 | — |
| Ethanol 96% denat | 22.40 | 22.40 | — |
| Perfume aloe vera 545 | 0.48 | 0.48 | — |
| Sodium sulfite, anhydrous | — | — | 0.05 |
| Polydimethylsiloxane 60000 cs | — | — | 0.50 |
| PEG-7 glyceryl cocoate | — | — | 0.50 |
| Water, demineralized | — | — | 1.00 |
| Phosphoric acid 85% | 0.032 | 0.032 | — |
| Xiameter ® MEM 0949 Emulsion | — | — | 2.00 |
| Dow Corning 959 | — | — | 1.00 |
| Hydrolyzed silk protein | — | — | 0.50 |
| Oil phase | 20 | 20 | |
| Cyclopentasiloxane | 15.0 | 15.0 | 4.5 |
| Trisiloxan fluid 1 cs | 5.0 | 5.0 | 3 |
| Total | 100 | 100 | 100 |

Explanation of the ingredients (other and/or INCI name):
Dehyquart ® A-CA INCI: Cetrimonium chloride
Dehyquart ® E-CA INCI: Hydroxycetyl hydroxyethyl dimonium chloride
Dehyquart ® SP INCI: Quaternium-52
Nutrilan ® Keratin W PP INCI: Hydrolyzed keratin
Gluadin ® WQ PP INCI: Laurdimonium hydroxypropyl Hydrolyzed wheat protein
Lamequat ® L INCI: Lauryldimonium hydroxypropyl Hydrolyzed collagen
Croquat ® WKPS-LQ-(WD) INCI: Steardimonium hydroxypropyl Hydrolyzed keratin
ProSina ® INCI: Hydrolyzed keratin
Xiameter ® MEM 0949 Emulsion INCI: Amodimethicone and cetrimonium chloride and trideceth-12
Dow Corning 959 INCI: Amodimethicone, Trideceth-12, Cetrimonium chloride The following smoothing treatment was carried out with the smoothing agents according to Examples 1 and 2:

Step 1: The hair was washed with a deep cleansing shampoo for 10 minutes.

Step 2: The hair was sprayed with the respective smoothing agent strand by strand without prior drying, and distributed with the aid of a comb (15 min). The hair was then blown dry (20 min) and treated with a straightening iron strand by strand (20 min). The total treatment time was thus approximately 65 min.

With the conventional creamy smoothing agent of Comparative Example 1, the following procedure was carried out:

Step 1: The hair was washed with a deep cleansing shampoo for 10 minutes and then blow dried for 16 min.

Step 2: The smoothing agent was applied to the hair stand by stand by employing brush and bowl (20 min). The hair was then blown dry (33 min) and treated with a straightening iron strand by strand (20 min).

Step 3: The hair was washed again with a care shampoo and after-treated with a conditioner (13 min). The hair was then blown dry (12.5 min).

The total treatment time was thus approximately 114.5 min.

Properties—Test results of Example 1 and Comparative Example 1 are summarized in the following table:

TABLE 2

|  | Example 1 | Comparison example 1 |
|---|---|---|
| Hair type | Dyed, slightly wavy, curled | |
| Consumption amount | 24.7 g | 41.7 g |
| Residues on hair and comb | no | yes |
| Blow dry duration | Faster in Example 1 | |
| Performing the smoothing | Comparable, somewhat better in Example 1 | |
| Smoothing result | Feel, combability, luster, anti-frizz and smoothing better in Example 1 | |
| Smoothing results after 18 washes | unchanged | unchanged |
| Smoothing results after 36 washes | Slight increase of the undulation | unchanged |
| Overall evaluation | better | worse |

A comparison of the results of the smoothing agents of Example 1 (with L-lysine) and Example 2 (without L-lysine) also showed a somewhat better smoothing result immediately after the smoothing as well as better combability and better feel for Example 1. These results were also confirmed after a conditioner treatment of the wet and dry hair.

Various creamy smoothing agents on the market were regularly observed after the smoothing treatment in the hair and on the comb, the consumption of smoothing agents was regularly lower, and the hair properties and the care result were overall better.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

What is claimed is:

1. A two-phase liquid agent for the non-chemical smoothing and de-curling of keratin fibers, having a pH value of from about 4 to about 6 and having an aqueous-alcoholic phase that is continuous and is present in an amount of about 80% by weight of the liquid agent and a non-aqueous phase that is continuous and is present in an amount of about 20% by weight of the liquid agent and wherein the aqueous-alcoholic phase and the non-aqueous phase exist separately from one another, the agent comprising:
   (a) at least one care substance liquid at 20° C. consisting of at least one protein hydrolyzate and/or derivative of a protein hydrolyzate, in a total amount of about 2.2 to about 2.5% by weight;
   at least one quaternary ammonium compound in a total amount of about 2.4 to about 2.5% by weight; and glycerine in a total amount of from about 1.6 to about 2.5% by weight,
   (b) ethanol in a total amount of from about 21 to about 25% by weight,
   (c) about 45 to about 55% by weight of water, and
   (d) cyclopentasiloxane and octamethyltrisiloxane, in a total amount of from about 18 to about 22% by weight,
   wherein:
   the liquid agent is free of solid fatty substances at 20° C.,
   the quantity value for each component is based on the total weight of the liquid agent, and
   the liquid agent is not an oil-in-water or water-in-oil emulsion.

2. The agent according to claim 1, wherein the agent has a viscosity (Brookfield RVDV-II+, 20° C., spindle 1, 100 rpm) of from 0 to about 2000 mPa·s.

3. The agent according to claim 1, which does not contain keratin-reducing substances.

4. The agent according to claim 1, which is made up as a spray.

5. The agent according to claim 1 further comprising lysine.

6. The agent according to claim 1, wherein the liquid agent comprises formaldehyde in an amount of no greater than about 0.05% by weight based on the total weight of the liquid agent.

7. The agent according to claim 5, wherein the liquid agent comprises the lysine in an amount of from about 0.01 to about 5% by weight based on the total weight of the liquid agent.

8. The agent according to claim 5 wherein the lysine is present in a total amount of about 0.8% by weight.

9. The agent according to claim 1 that consists essentially of (a)-(d).

10. The agent according to claim 1 wherein
   the at least one care substance liquid at 20° C. consists of at least one protein hydrolyzate and/or derivative of a protein hydrolyzate, in a total amount of about 2.2% by weight; at least one quaternary ammonium compound in a total amount of about 2.4% by weight; and glycerine in a total amount of about 1.6% by weight;
   the ethanol is present in an amount of from about 21 to about 22% by weight;
   the water is present in an amount of from about 48 to about 50% by weight; and
   the cyclopentasiloxane and octamethyltrisiloxane is present in a total amount of about 20% by weight.

11. The agent according to claim 10 further comprising lysine present in an amount of about 0.8% by weight.

12. The agent according to claim 11 wherein
   the cyclopentasiloxane is present in a total amount of about 15% by weight; and the octamethyltrisiloxane is present in a total amount of about 5% by weight.

13. The agent according to claim 10 wherein
the cyclopentasiloxane is present in a total amount of about 15% by weight; and
the octamethyltrisiloxane is present in a total amount of about 5% by weight.

14. The agent according to claim 8 that consists essentially of (a)-(d).

15. The agent according to claim 10 that consists essentially of (a)-(d).

16. The agent according to claim 12 that consists essentially of (a)-(d) and lysine, has a viscosity (Brookfield RVDV-II+, 20 ° C., spindle 1, 100 rpm) of from 0 to about 2000 mPa·s, and does not contain keratin-reducing substances.

17. The agent according to claim 13 that consists essentially of (a)-(d) and lysine, has a viscosity (Brookfield RVDV-II+, 20 ° C., spindle 1, 100 rpm) of from 0 to about 2000 mPa·s, and does not contain keratin-reducing substances.

18. A method for the non-chemical smoothing or de-curling of keratin fibers, the method comprising the steps of:
applying the liquid agent according to claim 1 onto the hair;
distributing the liquid agent in the hair;
drying the hair; and
smoothing the hair via mechanical and/or heating action.

19. The method according to claim 18 further comprising the step of washing the hair with a shampoo prior to applying the liquid agent.

20. The method according to claim 18 wherein a step of washing the hair is not performed after the step of smoothing the hair.

* * * * *